United States Patent
Wright et al.

(10) Patent No.: US 6,967,030 B2
(45) Date of Patent: Nov. 22, 2005

(54) FORMULATION FOR INSULIN AND GLUCOSE CONTROL

(76) Inventors: Jonathan V. Wright, 36338 32nd S., Auburn, WA (US) 98001; Wallace E. Block, 28 Dolores St., San Rafael, CA (US) 94901

( * ) Notice: Subject to any disclaimer, the term of this patent is extended or adjusted under 35 U.S.C. 154(b) by 0 days.

(21) Appl. No.: 10/342,843

(22) Filed: Jan. 14, 2003

(65) Prior Publication Data

US 2004/0137090 A1 Jul. 15, 2004

(51) Int. Cl.[7] .................. A61K 33/24; A61K 33/78; A61K 31/05
(52) U.S. Cl. ............... 424/655; 424/725; 424/729; 424/739; 514/730; 514/731; 514/732; 514/866
(58) Field of Search ................. 424/655, 725, 424/729, 739; 514/730, 731, 732, 866

(56) References Cited

U.S. PATENT DOCUMENTS

| | | | |
|---|---|---|---|
| 5,929,066 A | * | 7/1999 | McCarty .................. 514/188 |
| 6,258,848 B1 | * | 7/2001 | Fantus .................... 514/562 |
| 6,326,034 B1 | * | 12/2001 | Mirsky et al. ............ 424/725 |
| 6,376,549 B1 | * | 4/2002 | Fine et al. ............... 514/635 |
| 2002/0098247 A1 | * | 7/2002 | Komorowski et al. ...... 424/655 |

FOREIGN PATENT DOCUMENTS

CN    1346642    *   5/2002

OTHER PUBLICATIONS

Jarvill–Taylor et al. 2001. J. Am. College Nutrit. vol. 20 (4), pp. 327–336.*
Daily Telegraph, Aug. 10, 2000, US: Hoope for Diabetes Sufferers from Cinnamon. PROMT Abstract enclosed.*
Ohr, L. 2002. Food Technology. vol. 56 (9), pp. 87–92, FROSTI Abstract enclosed.*
Coghlan, A. New Scientist. 2000. vol. 167 (2251), FROSTI Abstract enclosed.*

* cited by examiner

*Primary Examiner*—Christopher R. Tate
(74) *Attorney, Agent, or Firm*—Jensen & Puntigam, P.S.

(57) ABSTRACT

The formulation includes a combination of a chalcone, specifically, methylhydroxychalcone polymer, in the amount of 6 mg to 24 mg, and chromium, in the amount of 500 mcg to 2000 mcg. The formulation also includes a plurality of vitamins and nutrients, vitamins $B_6$, C, E and K including green tea polyphenols and other nutrients.

6 Claims, No Drawings

FORMULATION FOR INSULIN AND GLUCOSE CONTROL

TECHNICAL FIELD

This invention relates generally to insulin and glucose control therapy and more specifically concerns a formulation for enhancing insulin sensitivity.

BACKGROUND OF THE INVENTION

Insulin control therapy in various forms is well known. Its primary use has been relative to treatment of type 2 diabetes. Type 2 diabetes is a common disorder characterized typically by several metabolic abnormalities, including insulin resistance and insulin deficiency. These abnormalities result in hyperglycemia, which can in turn result in cardiovascular morbidity and mortality. Glucose control will delay the onset and retard the progression of microvascular and possibly macrovascular disease in those individuals having type 2 diabetes.

Various techniques and treatments are known for glucose control. In one type of treatment, lifestyle changes are used to improve insulin sensitivity. These changes include weight loss, dietary change and exercise. As the disease progresses oral insulin secretagogues and insulin sensitizers are used, either separately or together, in order to maintain proper glucose levels. In the final stages of the disease, due to its progressive nature, including the progressive decline in pancreatic beta-cell function, insulin supplementation is usually required to achieve the desired glycemic goals. This treatment requires highly motivated patients. Many individuals with type 2 diabetes, however, cannot use insulin supplementation, including the elderly and those with co-morbid conditions. For these individuals, as well as other individuals with particular medical or physical limitations, insulin administration treatments are precluded.

For certain individuals, insulin is used along with oral antidiabetic medications to normalize glycemia. This has been an effective alternative to direct injection of insulin. This type of therapy is often effective for those individuals who show some responsiveness to oral anti-diabetic medications, but where those medications are not effective by themselves. This type of therapy, however, often results in the disadvantages of weight gain and hypoglycemia.

Other treatment alternatives include the use of continuous subcutaneous insulin infusion, and intraperitoneal systems. Still other treatment regimens include inhalation and buccal insulin preparations. However, all of the above therapies have disadvantages. The medications, for instance, which force the pancreas to make still more insulin have the risk of accelerating breakdown of the entire insulin regulatory system. Other side effects are of varying severity.

Hence, it would be desirable to have an insulin control treatment that is effective for a wide range of patients, yet have few or no side effects.

SUMMARY OF THE INVENTION

Accordingly, the present invention is an insulin and glucose control formulation, comprising: methylhydroxychalcone polymer (MHCP); and chromium, in therapeutically effective amounts, respectively.

BEST MODE FOR CARRYING OUT THE INVENTION

As discussed above, treatment for diabetes by improving insulin sensitivity is typically divided between life style changes on the other hand, and drug therapy on the other hand, although both types of treatment have been used together. In the present invention, however, nutritional therapy is used to produce a third treatment alternative which has been found to slow the decline to final stage type 2 diabetes. The present invention involves a new formulation that mimics the effect of insulin in the human body, specifically a combination of 1) methylhydroxychalcone polymer (MHCP) a compound found in cinnamon and 2)chromium. Other nutrients can be added to this combination, as discussed in more detail below. The formulation is prepared for ingestion in oral form.

MHCP is one part of the present formulation. It has been discovered that the nutrient MHCP can stimulate glucose uptake by body cells, and even in some cases assisting in the synthesis of glycogen, which is a polymer of glucose produced by the body to store energy. When needed, such as during exercise, glycogen is depolymerized back to glucose. Most gylcogen is found within the liver but also in some muscles where it is mobilized when quick energy is needed. MHCP helps in this synthesis production of glycogen.

Both of the above characteristics are insulin-related fuctions that help maintain healthy blood sugar levels. MHCP has similar effects to insulin in that it chemically modifies the individual cells' insulin receptors in such a way to permit glucose molecules to pass through the cell wall into the interior of the cell, where the glucose is used for energy production. The series of molecular events initiated by insulin's interaction with its receptor, known as insulin cascade, is also initiated or triggered by MHCP.

MHCP also has a synergistic effect on the insulin already present in the body. MCHP thus has its own separate effect relative to type 2 diabetes but also enhances the body's own insulin.

The amount of MHCP in the present formulation is in the range of 6–24 milligrams (mg) as a daily dose for effective therapeutic results.

In addition to its effect on insulin control relative to diabetes discussed above, MHCP has been found to reduce blood pressure and also to reduce or prevent the formation of oxygen radicals, an antioxidant effect, which has been shown independently to reduce the progression of various complications of diabetes.

The other part of the present formulation is chromium, which is known to improve blood sugar regulation by itself for type 2 diabetes. In the present formulation, 500 to 2000 micrograms (mcg) of chromium in a daily dose has an effective therapeutic effect, with 1000 mcgs (1 milligram) being preferred.

The combination of MHCP, in an amount in the range of 6–24 mg and chromium in an amount in the range of 500 to 2000 mcgs, as a daily dose, produces a therapeutic effect relative to delaying the onset and retarding the progression of type 2 diabetes. The two elements are combined together in an oral dose.

As indicated above, additional nutrients can be added to the above combination to further enhance the insulin control effect. In one instance, green tea extract, specifically polyphenols EGCG, enhance the operation of insulin in the body. The green tea polyphenols are powerful natural phytochemical antioxidants, and act as scavengers of free radicals. They also chelate transition metal free radical catalysts such as iron. The therapeutically effective amount of ECGC in the present formulation is 120–480 mg.

Other nutrients, which can be added to the formulation include various vitamins, including vitamin $B_6$, vitamin C, vitamin E and vitamin K. In one embodiment, 10 mg of vitamin $B_6$ is used, 200 mg of vitamin C, 90 mcg of vitamin K and vitamin E 100 IU.

Additional ingredients include alpha-lipoic acid (an antioxidant) goat's rue (galega officinalis, an herbal extract), quercetin (a favonoid), N-acetylcysteine (an amino acid derivative) and the mineral vanadium. One embodiment includes 600 mg of alpha lipoic acid, 20 mg of goat's rue, 75 mg of N-acetylcysteine, 75 mg of quercetin and 1 mg of vanadium.

While the above additional nutrients promote, in one way or another, healthy blood sugar levels, they are in addition to the basic formulation of the present invention which comprises MHCP and chromium. In addition, the amounts of the nutrients specified above may vary.

Hence, the present invention is a new formulation of MHCP and chromium, in the therapeutically effective amounts set forth above, which aids in the control of insulin and glucose, and more specifically is useful in the treatment of or to prevent the onset of type 2 diabetes.

Although a preferred embodiment of the invention has been disclosed for purposes of illustration, it should be understood that various changes, modifications and substitutions might be incorporated in the embodiment without departing from the spirit of the invention, which is defined by the claims, which follow.

What is claimed is:

1. An insulin and glucose control daily dose formulation for treatment of humans, comprising:
   methylhydroxychalcone polymer (MHCP) in an amount within the range of 6–24 mg; and
   chromium, in an amount within the range of 500–2000 mcgs, wherein the amount of MHCP and the amount of chromium are in combination therapeutically effective.

2. The formulation of claim 1, wherein the formulation is in an oral dose form.

3. The formulation of claim 1, further comprising green tea polyphenols in the amount of 120 mg to 480 mg.

4. The formulation of claim 1, further comprising one or more of the following vitamins: vitamin $B_6$, vitamin C, Vitamin E and Vitamin K.

5. The formulation of claim 1, further comprising one or more of the following nutrients: goat's rue (galega officinalis), quercetin N-acetylcysteine, alpha-lipoic acid and vanadium.

6. The formulation of claim 1, wherein the amount of MHCP is 12 mg and the amount of chromium is 1 mg.

\* \* \* \* \*